United States Patent [19]

Cais et al.

[11] 4,456,690

[45] Jun. 26, 1984

[54] NON-CENTRIFUGATION METHOD FOR IMMUNOASSAY OF MATERIALS

[75] Inventors: Michael Cais; Moshe Shimoni, both of Haifa, Israel

[73] Assignee: Technion Research and Development Foundation, Ltd., Technion City, Israel

[21] Appl. No.: 393,397

[22] Filed: Jun. 29, 1982

[30] Foreign Application Priority Data

Jul. 20, 1981 [IL] Israel ............................................ 63363

[51] Int. Cl.³ .................... G01N 33/58; G01N 35/00; G01T 1/00

[52] U.S. Cl. ............................... 436/500; 436/510; 436/538; 436/541; 436/800; 436/801; 436/804; 436/809; 436/810; 436/817; 436/824; 436/808

[58] Field of Search .................... 424/1, 1.5; 422/61; 436/500, 541, 800, 804, 808, 809, 810, 817, 824, 510, 538, 801; 435/4, 7

[56] References Cited

U.S. PATENT DOCUMENTS

| | | | |
|---|---|---|---|
| 2,524,362 | 10/1950 | Smith | 128/220 |
| 3,068,855 | 12/1962 | Furlong, Jr. | 422/61 |
| 3,449,081 | 6/1969 | Hughes | 422/61 |
| 3,992,150 | 11/1976 | Retzer | 422/61 |
| 4,021,352 | 5/1977 | Sarstedt | 210/359 |
| 4,071,319 | 1/1978 | Nugent | 422/61 |
| 4,087,248 | 5/1978 | Miles | 424/1 |
| 4,197,287 | 4/1980 | Piasio et al. | 424/1 |
| 4,235,865 | 11/1980 | Thoma | 424/1 |
| 4,254,082 | 3/1981 | Schick et al. | 422/61 |

*Primary Examiner*—Christine M. Nucker
*Attorney, Agent, or Firm*—Schwartz, Jeffery, Schwaab, Mack, Blumenthal & Koch

[57] ABSTRACT

The present invention relates to a method which eliminates centrifugation and decantation steps, to be performed in an automatic manner for carrying out specific binding assay tests, wherein liquid and solid phases are present.

According to the invention, use is made of a specially designed device, consisting of a mixing reservoir into which is fitted snugly a mixer separator having a channel in the vertical axis of the mixer-separator. A rack holding a number of said mixing reservoirs containing the incubated reagents and analytes, capped with the mixer separators, is placed into a press-device designed to perform at a controlled rate a downward movement. The mixer separators are pushed downwards into the mixing reservoirs at a chosen rate for a preselected distance to complete the mass transport and separation operations. The separation devices are removed and either one of the separated phases can be measured in the desired analytical instrument for a quantitative or qualitative determination.

The results obtained according to the present invention compare very favorably with those determined by other methods requiring centrifugation and/or decantation in the assay protocol.

22 Claims, 7 Drawing Figures

NON-CENTRIFUGATION METHOD FOR IMMUNOASSAY OF MATERIALS

BACKGROUND OF THE INVENTION

The present invention relates to an improved method for carrying out specific binding assay tests. More particularly the invention relates to an improved method to be performed in an automatic manner for carrying out specific binding assay tests wherein liquid and solid phases are present.

As known, specific binding assays are based on the principle of monitoring specific binding reactions, in which the extent of binding is a function of the amount of unknown ligand present, by means of a labelled component. Among the known methods the following specific binding assay techniques can be mentioned: Radioimmunoassay (RIA), metalloimmunoassay (MIA), free radical assay technique (FRAT), hemaglutination inhibition (HI), enzyme multiplied immunoassay technique (EMIT), fluorescence immunoassay (FIA) and luminescence immunossay (LIA). In some of these techniques (RIA, MIA, FIA, LIA) the mixture comprising the unlabelled ligand, labelled ligand and antibody is allowed to reach an equilibrium and the antibody-bound ligand is separated from the free ligand. In the radiomunoassay, the ligand or the antibody is labelled with a radioactive isotope, whereas in the metalloimmunoassay the ligand is labelled with a metal-containing reagent which contains also a suitable functional group by means of which one can attach the metal reagent to the hapten desired to be assayed. A full description of the latter is given in our previous U.S. Pat. No. 4,205,952. In FIA the label is a fluorescent compound and in LIA the label is chemiluminescent or bioluminescent agent.

The operation of separating the free fraction from the bound one, is of great importance and its accuracy determines the sensitivity and precision of the entire specific binding assay technique. In selecting and assessing a separation operation, it is useful to consider the criteria that should be fulfilled in order to obtain the desired result. The following major requirements of an ideal separation can be mentioned:

(i) It should completely separate bound and free fractions, with a wide margin for error in the conditions used for separation;
(ii) It should not interfere with the primary antigen-antibody binding reaction;
(iii) It should be simple, easy and rapid to use;
(iv) It should be inexpensive and use reagents and equipment that are readily available;
(v) It should not be affected by plasma or serum;
(vi) All manipulations should be performed in a single tube;
(vii) It should be suitable for automation;
(viii) It should be applicable to a wide range of antigens;
(ix) The manipulative steps in radioimmunoassays should be designed so that they ensure maximum safety from radiation hazards resulting from handling the radioactive reaction system.

A critical review of the variety of methods available and the extent to which each method approaches all or any of the ideal requirements mentioned above is beyond the scope of this specification. The most widely used techniques mentioned by the prior art are adsorption methods (charcoal, silicates), fractional precipitation methods (ammonium sulphate, ethanol, dioxan, polyethylene glycol), double antibody methods and solid phase methods (immunoadsorbants), all of which end up with a system of suspended particles in a liquid medium. The selection of any particular technique is determined by consideration of many interrelated factors such as solubility of compound, characteristics of antiserum, fraction to be counted, degree of non-specific binding, type of radioisotope. However one feature which is common to all of the above methods is the need for a centrifugation step to effect aggregation of the suspended solid particles followed by a decantation (or suction) step to physically separate the solid and liquid phases.

In a previous patent application (Ser. No. 124,691 assigned to Technion Research & Development Foundation Ltd., it has been disclosed a method to be used in specific binding assay, wherein the separation of the bound fraction from the free fraction is carried out by solvent extraction technique, using organic solvents as extractants. In another prior patent application (Ser. No. 212,806 in the names of M. Cais, M. Shimoni and Technion Research & Development Foundation Ltd. a newly designed device designated as "LIDEX" for carrying out said technique of solvent extraction has been described. According to said invention, the "LIDEX" device consists of a mixing-reservoir (A) into which is fitted snugly a mixer-separator (B), having a channel in the vertical axis of the mixer-separator. The two substantially immiscible liquid solutions are introduced into the mixing reservoir, the phases are thoroughly mixed by moving the mixer-separator (B) in and out the mixing-reservoir (A). After the spontaneous separation into an upper and lower phase, the upper phase is removed by pushing in the mixer-separator, said upper phase being accumulated in a collecting container (E).

In another prior patent application (Ser. No. 270,411) in the names as in the previous one, mass transport separations for various purposes including specific binding assays, to be carried out through selective barriers, have been disclosed. The invention discloses a new "Lidex" device similar to that described in the U.S. patent application Ser. No. 212,806 a barrier being located in the mixer-separator. The resistance raised to the flow of the liquid phase through the membrane into the mixer-separator will generally cause a penetration of the fluid arround the sealing element located on the mixer-separator, during the downward gliding of the mixer-separator, which of course will completely interfere the assay. In order to remedy said difficiency, the device is provided with means for accumulating of gas pocket such as one or more horizontal, vertical or spiral grooves on the mixer separator in which the air located therein, will decrease the pressure exerted on the barrier so that said penetration of the fluid arround the sealing element is avoided. The invention was found to give excellent results in various systems and for different membranes and types of solvents and/or precipitates.

One of the main requirements encountered in immunoassay, is the reproducibility of the results with a minimal deviation between two duplicates, which implies a complete standardization of the procedure with minimal handling and manual working without depending on extraneous factors. An example of such an extraneous factor is the extent of mixing of the phases in the assay. Another extraneous factor is the rate of separating the desired phase which has to be subsequently analysed.

In the Lidex device without a barrier, used in immunoassay, the test requires a vigorous and thorough agitation to enable a complete mass transfer and an accurate separation between the two liquid phases. As will be realized, the agitation obtained by manual moving the mixer-separator (B) in and out the mixing-reservoir (A), can not be interpreted quantitatively, being actually of a subjective character according to the technician performing the immunoassay. The problem is even more complicated in the case of Lidex device with a membrane, when any different system may necessitate a specific membrane and/or solvent and accordingly will require diverse extent of mixing and/or different rate of separation. This of course will be very difficult or even impossible by a manual handling, particularly for immunoassay, when high accuracy with the closest possible reproducible results are required. Even a technician versed in the art of immunoassay, could hardly assure that a complete mass transfer was accomplished after a certain agitation period. On the other hand, a prolonged agitation might interfere with easy phase separation, when two liquids are involved, or causes damage to the membrane, when precipitates are present.

SUMMARY OF THE INVENTION

It is an object of the present invention to provide an improved method for carrying out the immunoassay technique. It is another object of the present invention to provide an improved method for carrying out the immunoassay technique which eliminates both the centrifugation and decantation manipulations. It is yet another object of the present invention to provide an improved method for carrying out the immunoassay technique, which eliminates the subjective determination on the extent of agitation and improves the phase separation. It is yet another object of the present invention to provide an improved method for carrying out the immunoassay technique which avoids the laborious manual method for thorough mixing required for an efficient mass transfer. Thus, the invention consists of an improved method for carrying out the immunoassay technique in a special designed device consisting of a mixing reservoir into which is fitted snugly a mixer-separator having a channel in the vertical axis of the mixer-separator, which consists in the combination of the following steps:

(a) arranging the mixing reservoirs in a rack specially designed to hold a number of said mixing reservoirs with the mixer-separators;

(b) introducing the reagents and analytes into said mixing-reservoirs;

(c) capping said mixing reservoirs with said mixer-separators;

(d) allowing the reagents and analytes to incubate for a required period of time in above mixing reservoirs capped with the mixer-separators;

(e) placing the rack carrying the above separator devices with the incubated reagents and analytes into a press-device specially designed to perform at a controlled rate a downward movement whereby the mixer separators are pushed downwards into the mixing reservoirs at a chosen rate and for a preselected distance to complete the desired mass-transport and separation operation;

(f) operating the downward movement of said press-device at the preselected rate and distance;

(g) removing the rack upon the disengagement of the press-device; and (h) placing the separator devices into the desired analytical instrument for a quantitative or qualitative measurement of either one, or both, of the separated phases as required.

The method is very simple to carry out being characterized by the absence of any centrifugation and decantation steps, the whole operation taking place in a single tube-device. Moreover the results obtained by the method according to the present invention compares very favourably with known methods as described in the prior art.

DETAILED DESCRIPTION OF PREFERRED EMBODIMENTS

Figure 1A:
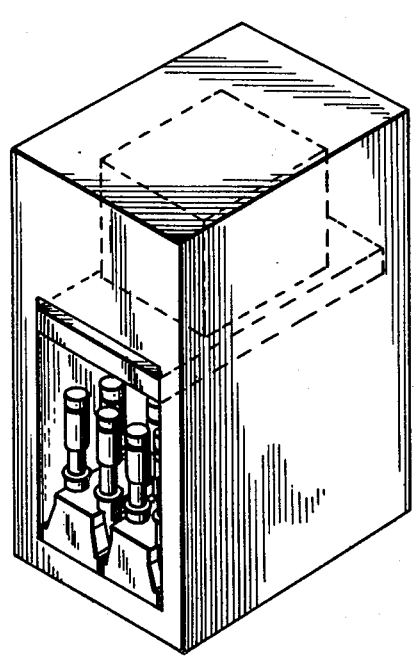
FIGS. 1a and 1b are schematic perspective views of the press-device used according to the present invention, in its upper and lowered positions.
Figure 1B:
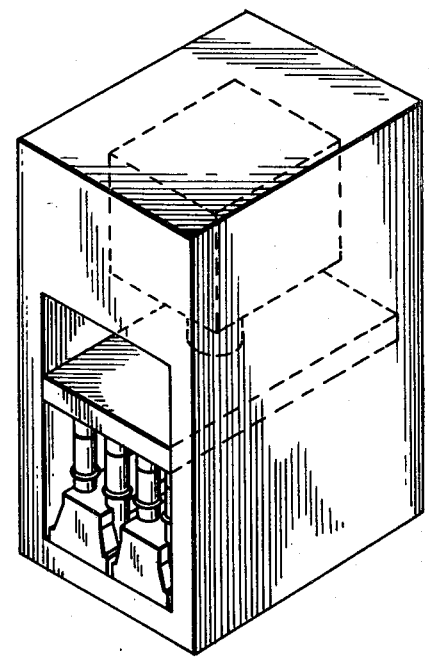

One of the elements which enables the performance of the method according to the present invention is the press-device utilized in step (e), referred to in the present specification as pressomat. Actually, the manual operation in steps (e), (f) and (g) is very simple and can be easily carried out by a technician in a laboratory where a relatively small number of tubes per assay are involved. However, since each tube has to be handled individually, this operation can be time-consuming in a routine laboratory performing a large number of analyses. Also a standardization of the procedure would be most desirable in order to ensure a complete non-dependency from extraneous factors. Various prototypes of the Pressomat based on either a pneumatic mechanism or an electrical motor have been found equally satisfactory. FIG. 1a shows the Pressomat at the start of the separation, with two test-tube racks, in place, each holding 20 Lidex devices. FIG. 1b shows the same instrument at the end of the operation, when the separators B in all 40 tubes have been pushed down by the moving platform to the required terminal position and the stoppers S in all separators have hermetically closed all the collecting containers E. The latter step takes place only in the final stage of the downward movement of the pressing platform, in order to allow escape of the displaced air in the Lidex separator. Upon completion of this operation (timed in our experiments for a total of less than 3 minutes) the pressing platform automatically reverses direction of movement and returns up to the starting position of the instrument. The test-tubes racks can be removed from the Pressomat to be taken to the counter as soon as the upward movement (indicated on the LED display) commences.

The pressomat (FIG. 1) is built in the form of a closed press in which the movement of the platform (pressing plate a) is produced by a motor linked to a travelling plate which presses on the Lidex separators in the racks (b) by direct contact. The body of the pressomat bears the streching strains produced as a result of the pressure being exerted during operation. The motor can be pneumatic, hydraulic, a pneumatic-hydraulic combination, or electric and can be linked either directly, or through a transmission system to the travelling plate. The motor is provided with a movement control mechanism (not shown in the Figure) which allows for adjustment of the speed of descent or ascent of the travelling plate according to the requirement of the operation. The operation of the pressomat is very simple: Upon pressing the start button, the travelling plate begins its downward movement and starts pressing on the Lidex separators at a predetermined rate of descent and preselected pressure. When the platform (a) reaches its predetermined lowest point (FIG. 1b) of descent it initiates the operation of a delay mechanism which keeps the platform in that position for a required and predetermined time period in order to complete the equal closure of all the Lidex separators in the test tubes racks (b) previously introduced in the pressomat. Upon completion of this delay time, the pressing plate (a) disengages from the Lidex separators and begins its movement in the upper direction at a desired speed and returns to the starting position (FIG. 1a). At this stage the pressomat is ready for the next operation.

Figure 2A:
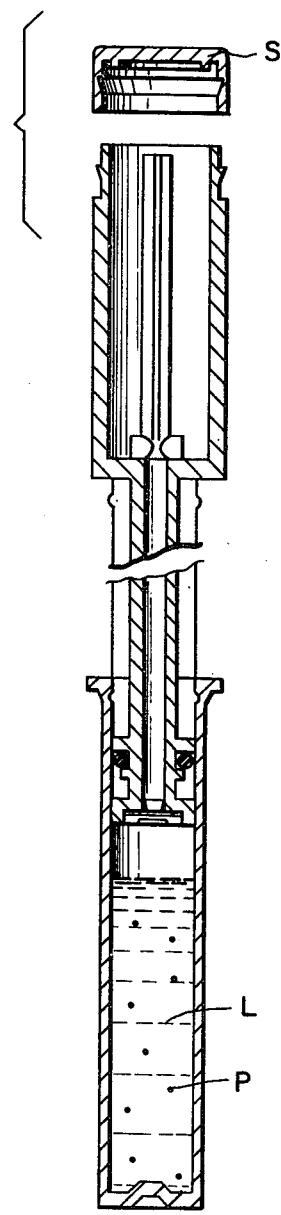
FIGS. 2a and 2b are cross-sectional views of the separators used according to the invention, both prior to and after the separation step is carried out.
Figure 2B:
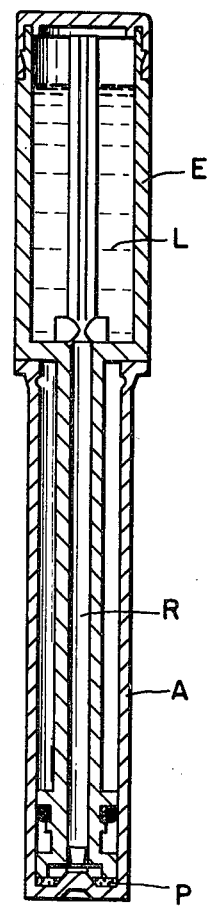

FIG. 2 is a schematical representation of the Lidex PS separator particular useful for immunoassay at the start (2a) and the end (2b) of the separation operation. The solid particles (P) initially suspended in the liquid phase (L) are fully separated and retained at the bottom of the mixing-reservoir A. The additional feature of the system shown in FIG. 2C is the plastic rod R placed in the axial channel C of the separator B. The purpose of this rod is to displace its volume equivalent of the liquid phase up into the collecting container E. The dimensions of the rod are such that there should be no interference with the free flow of the liquid phase in its passage through channel C, whilst at the same time only an insignificant amount of liquid will remain in the channel C at the end of the separation. As a result, the radioactivity partitioned between the solid and liquid phases can be physically separated practically in toto. This, together with the hermetical sealing by the stopper S provides an important added flexibility to the assay protocol. With gamma-emitting tracers it is possible to count at choice both a solid phase and/or the liquid phase simply by placing the separator in the well of the counter in the normal or upsidedown position respectively.

Figure 3:
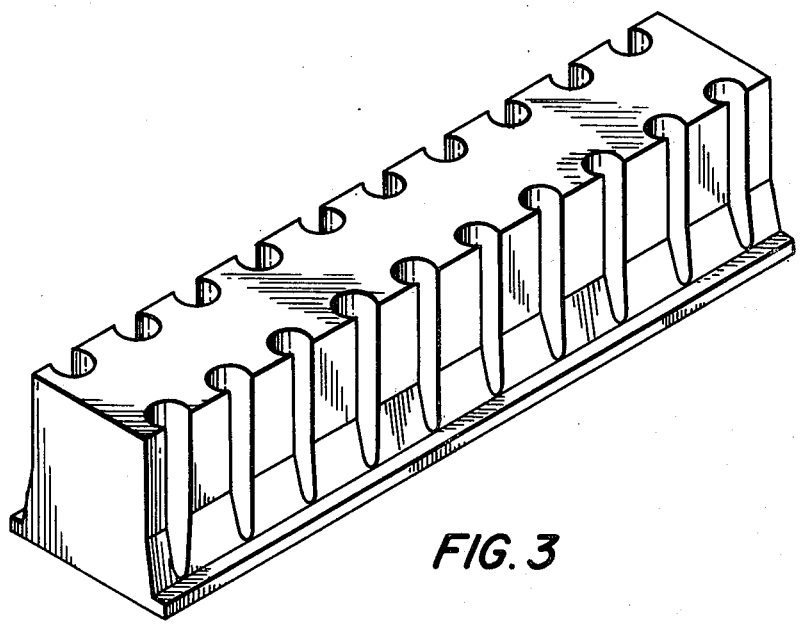
FIG. 3 is a perspective view of the holding tray used in the invention.

FIG. 3 shows an illustration of the rack with the devices, designed to allow for a maximum visualization of the mixing reservoirs A during the manual pipettation steps of the assay, and to fit properly in the Pressomat instrument.

The assay protocol using the Lidex PS separator methodology as described in the specification consists of the following:

(i) A series of mixing reservoirs A, in duplicates, were placed in the test-tube racks and assay reagents, standards and clinical samples were added as per kit instructions;

(ii) The mixing reservoirs were allowed to stand for the prescribed primary incubation time;

(iii) The precipitating (or adsorbing) reagent for the assay was added, ensuring that total reaction volume was 1.5–2.0 ml;

(iv) The separators B, fitted with the O-ring, membrane M, disc D, rod R and slightly capped with stopper S, were introduced into the tubes A, as shown in FIG. 2(a) and allowed to stand for second incubation (if the latter was not required by the assay, one proceeded directly to next step);

(v) Two test-tube racks (FIG. 3) holding the Lidex separators were placed into the Pressomat and instrument operation was started;

(vi) Upon completion of the operation (3 minutes) mixing reservoirs racks were removed from the Pressomat and the Lidex separators were transferred to the counter.

The problem encountered by diagnostic laboratories carrying out competitive protein binding analyses is many-faceted. Thus, they must cope with a large throughput of samples sent from several sources; interpret the significance of the results for the less experienced clinician; provide a wide range of determinations; return results quickly; and, above all, ensure that each assay is accurate. This must be done despite the economic difficulties encountered with a technique that is labour intensive, complex and expensive compared with some other forms of assay employed in clincial biochemistry. The increasing availability of RIA reagents in commercial kits may alleviate some of these problems, provided the analyst can rely on the quality of the reagents and the accuracy of the assay protocol. Given reagents of high quality, the separation of bound and free becomes, in our opinion, the most important step in the assay procedure. The efficacy of the new methodology according to the present invention, based on the Lidex PS separating device and the automatization features imparted by the Pressomat instrument (FIG. 1) have been tested with some of the most widely used separating reagents systems in commercially available kits.

The commercial $^{125}$I-RIA kits, selected so as to provide a variety of commonly used separating reagents, all requiring centrifugation and decantation in the kit protocol, were grouped into four categories, according to the separating reagent: (a) double-antibody (DAB) (Prolaction and FSH kits); (b) double antibody/polyethylene glycol (DAB/PEG) (ferritin, estriol, cortisol, testosterone, progesterone, $\beta$-hCG, insuline and hPL kits); (c) solid phase (insolubilized T$_4$-antibody); (d) activated charcoal (digoxin kit).

All these provide evidence for the feasibility and potential of the no-centrifugation Lidex separation methodology. It is important to emphasize that all the results presented herein were obtained without any prior work to optimize the adaption of the commercial kit reagents for use with the Lidex PS separator device. In cases where experiments were performed with high quality reagents and carried out optimization of the Lidex assay protocol (incubation time, reaction volumes, precipitating reagent), the results of the assay with Lidex PS methodology compared very favourably with those obtained from the commercial kit assay protocol.

Preliminary results indicate that with suitable cut-off membranes it might be feasible to use the Lidex separator device immediately subsequent to the primary incubation step, without requiring the addition of a precipitating or adsorbing reagent.

In the preamble of the specification there are enumerated the main requirements of an ideal separation technique, as formulated by the prior art. On the basis of the results obtained, the methodology according to the present invention will possess the following advantages;

(i) completely, or very nearly so, separates bound and free fractions with a wide margin for error in the conditions used for separation;
(ii) it does not interfere with the primary antigen-antibody binding reaction;
(iii) it is simple, easy and rapid to use;
(iv) it is inexpensive and uses reagents and equipment that are (or can become) readily available;
(v) it is not affected by plasma or serum;
(vi) all manipulations are performed in a single tube-separator device;
(vii) it is highly suitable for automation;
(viii) it is applicable to a wide range of antigens;
(ix) the methodology and design of the separator device practically eliminate potential contact with the radioactive reaction mixture thus ensuring maximum safety from radiation hazards.

While the invention has been described with specific embodiments thereof, it will be understood that it is capable of further modifications, and this patent is intended to cover any variation, uses or adaptations of the invention and including such departures from the present disclosure as come within known or customary practice in the art to which the invention pertains and as may be applied to the essential features hereinbefore set forth and as fall within the scope of the invention. In order to further illustrate the nature of this invention and the manner of practising it, the following Examples are presented for clearness of understanding only and no limitation should be understood therefrom.

EXAMPLES

The methodology according to the present invention was used in conjunction with the following separating reagents:
(a) double-antibody;
(b) double-anitbody/PEG;
(c) solid phase assay, and
(d) activated charcoal.

Figure 4A:
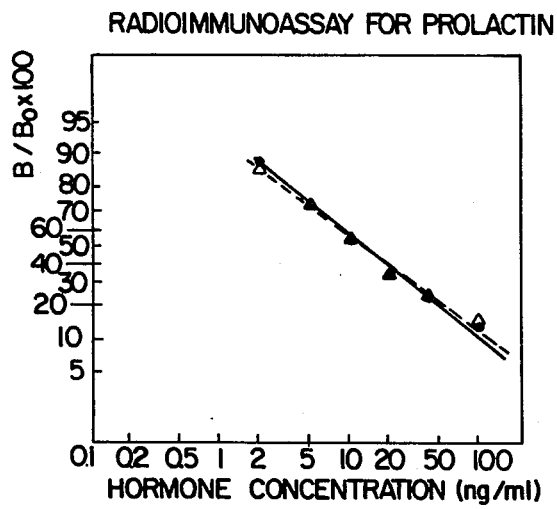
FIGS. 4–7 are standard curves for radio immunoassay of the listed species.
Figure 4B:
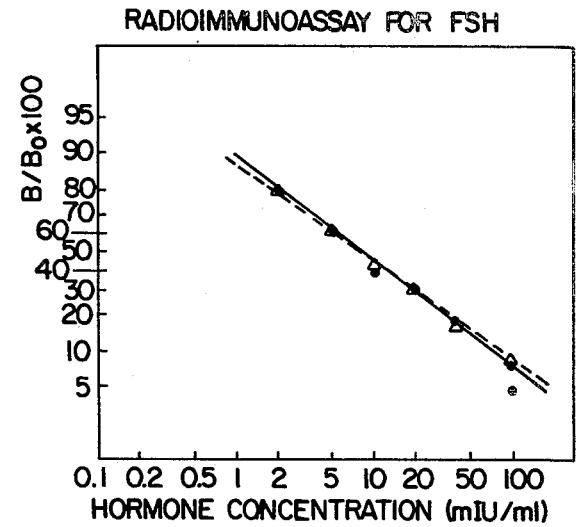
Figure 4C:
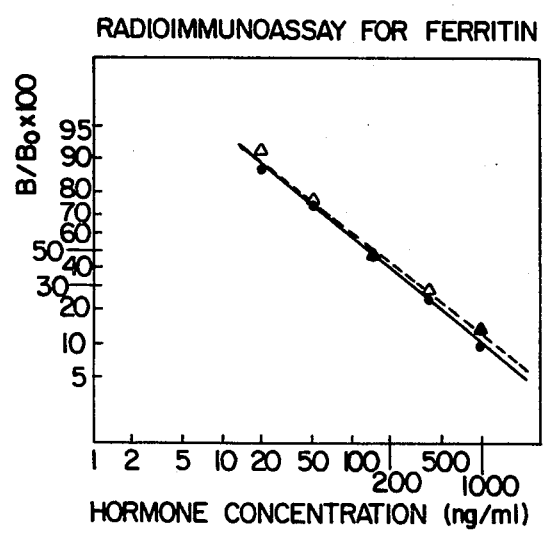
Figure 4D:
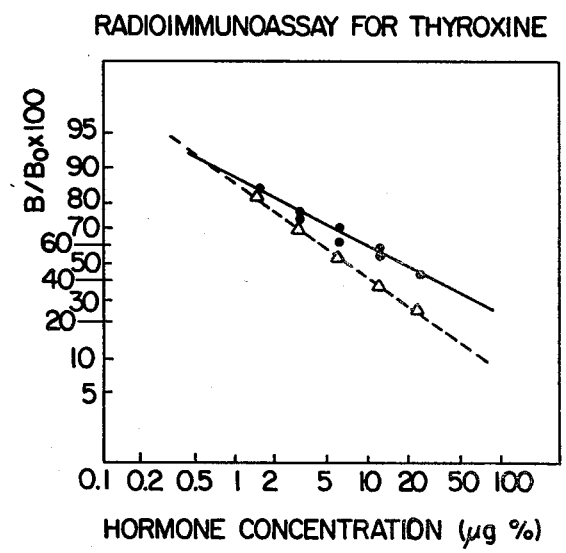
Figure 5A:
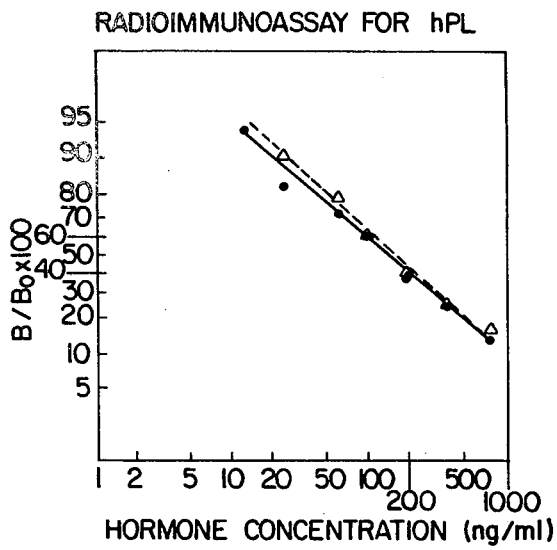
Figure 5B:
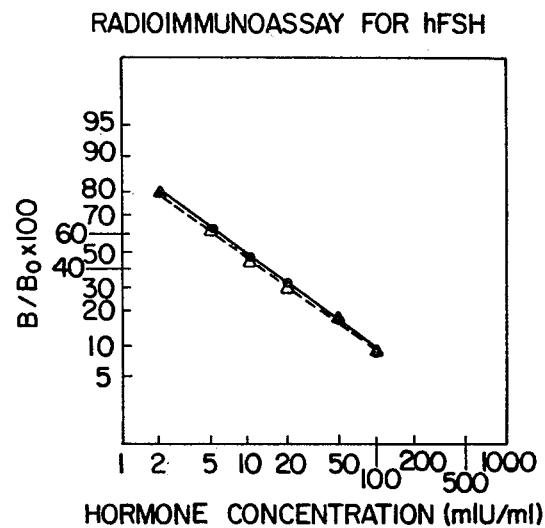
Figure 5C:
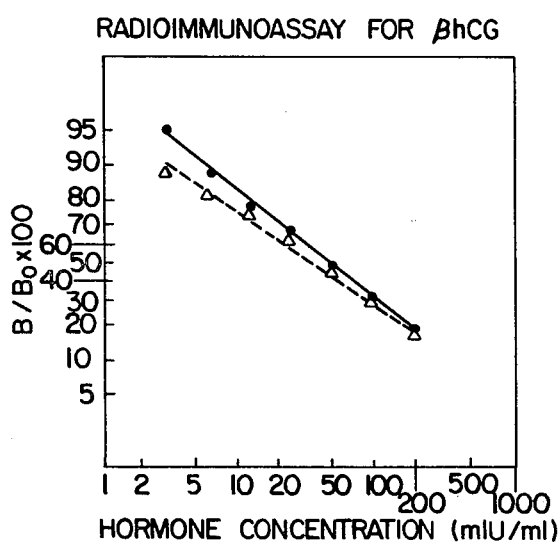
Figure 5D:
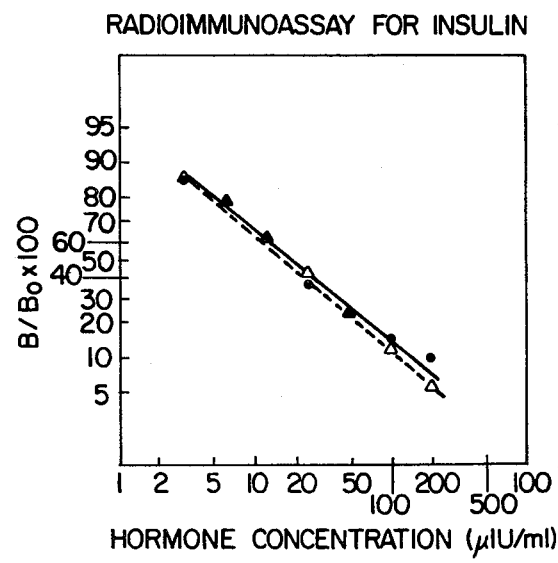
Figure 6A:
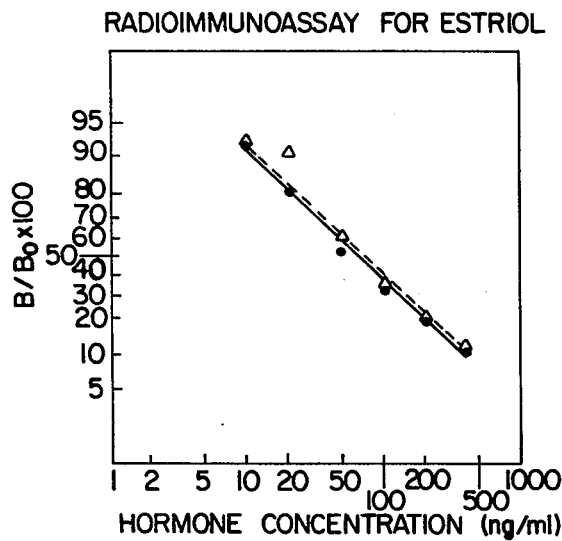
Figure 6B:
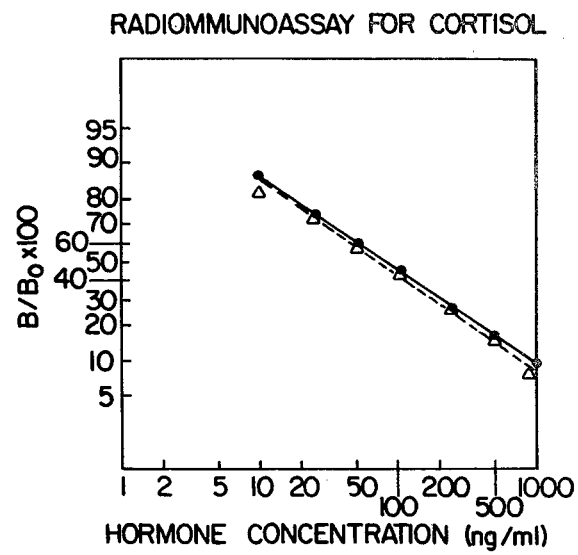
Figure 6C:
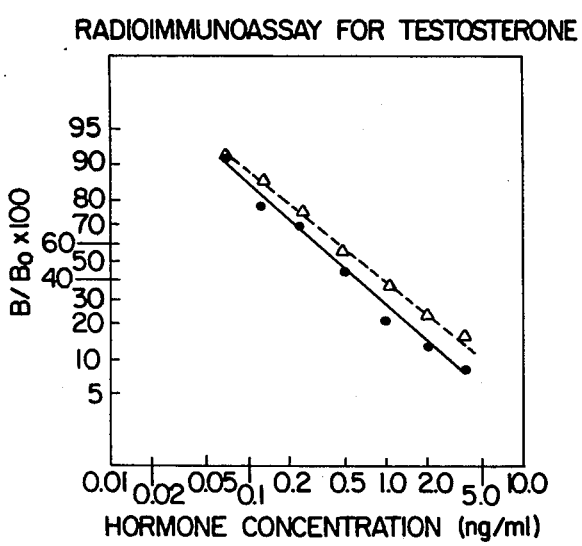
Figure 6D:
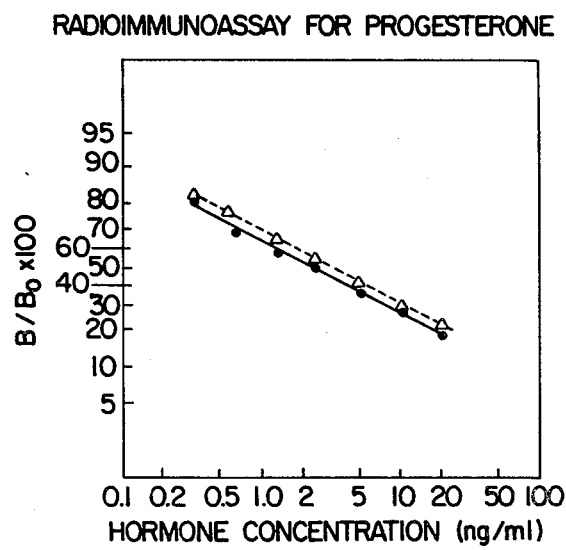
Figure 7A:
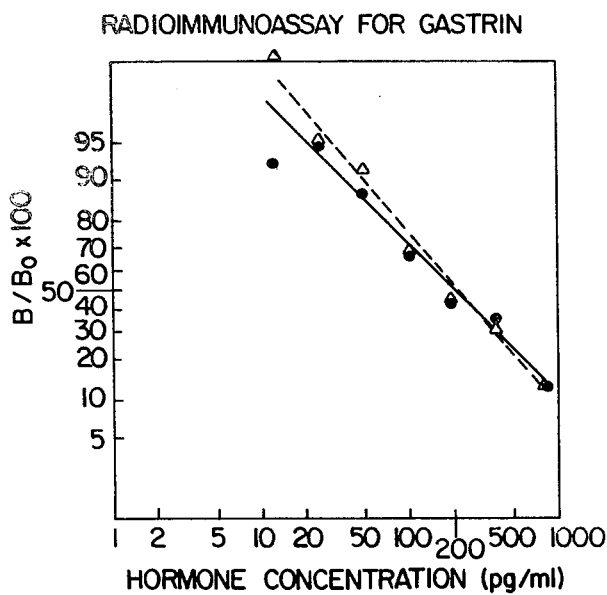
Figure 7B:
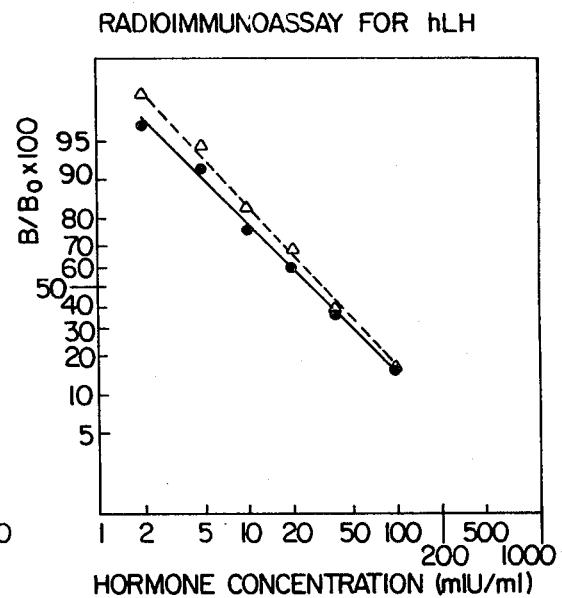
Figure 7C:
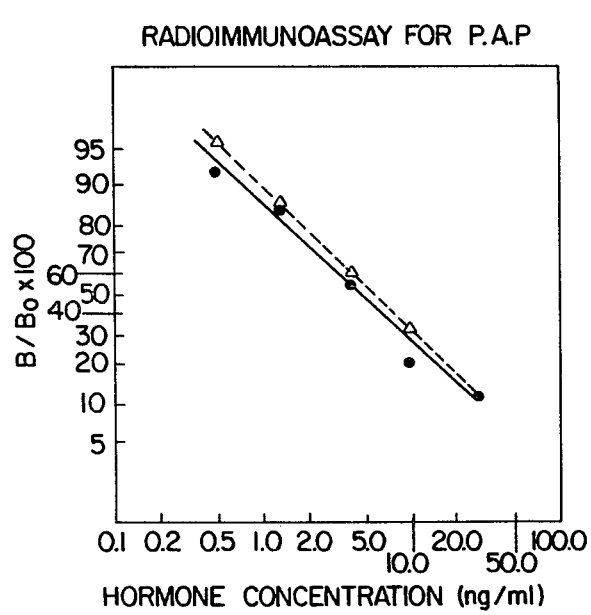
Figure 7D:
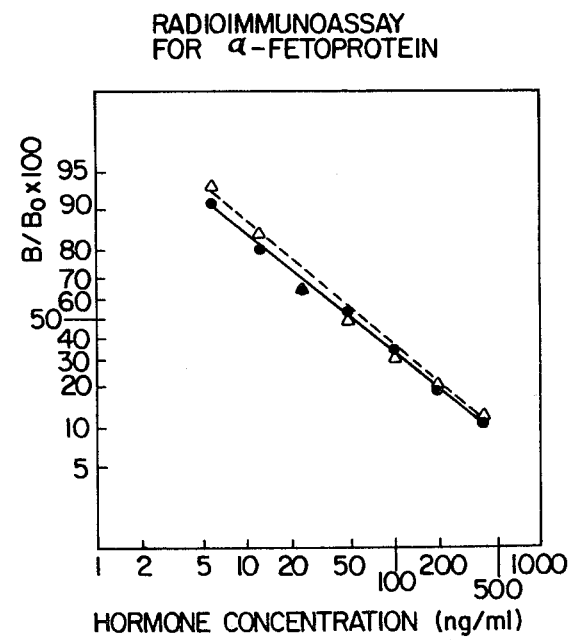

In each case, at least two experiments were carried out in parallel: one experiment was performed exactly according to the kit instructions, including centrifugation and decantation steps; in the other experiment the kit instructions were used with regard to addition of reagents, standards, clinical samples and incubation times, except that Lidex PS separators, test-tubes and the Pressomat instrument were used for separation of bound and free. In addition, total reaction volumes were adjusted as necessary:
(a) the standard curves obtained for $^{125}$I-FSH and $^{125}$I Prolaction (HPRL) assays are shown in FIGS. 4b and 4a respectively. The clinical sera values detained in the two assays are compared in Tables 1 (FSH) and 2 (HPRL). Double antibody (goat antirabbit I$_g$G) was the precipitating reagent.
(b) Double-antibody/PEG (20%) was used as precipitating reagent for the $^{125}$I ferritin assay which produced the standard curves shown in FIG. 4c and clinical sera values collected in Table 3. The use of the precipitating system required two pipettations and an additional incubation of 15 minutes (after addition of double antibody). It was found that a single pipettation of a premixed double anti-body/PEG (8%) reagent produced immediate precipitation at room temperature and no secondary incubation was necessary. The efficacy of this reagent in conjunction with Lidex separators methodology is demonstrated in a similar manner by the standard curves obtained for $^{125}$I estriol (FIG. 6a), cortisol (FIG. 6b), $^{125}$I-testosterone (FIG. 6c), $^{125}$I-progesterone (FIG. 6d), $^{125}$I-$\beta$HCG (FIG. 5c), $^{125}$I-insuline (FIG. 5d), $^{125}$I-hPL (FIG. 5a), hFSH (FIG. 5b), Gastrin (FIG. 7a), hLH (FIG. 7b), P.A.P. (FIG. 7c) and alpha FETO protein (FIG. 7d).

(c) The Lidex separator methodology is eminently suitable for use with solid phase immunoassays. An example is shown for a $^{125}$I-thyroxine solid phase assay (immobilized antibody). The standard curves are shown in FIG. 4a. Even though the two curves (kit method and Lidex method) are not as nearly superimposable as in the previous examples, the clinical sera values as calculated from their respective curves are nearly identical (Table 4).

(d) The use of activated charcoal as adsorbing reagent in conjunction with Lidex separation methodology was demonstrated with a $^{125}$I digoxin kit. In this example three parallel experiments were carried out in which the results obtained by following exactly the kit instructions (with 20 minutes centrifugation and decantation) were compared with those resulting from an assay using a solvent extraction method with Lidex LS separators and one using the new lidex PS separators, with selective barrier. In the latter experiment, the bound fraction transported with the liquid phase into the collecting container E of the separators was counted by placing upside-down the capped Lidex PS separators into the well of the counter. The standard curves for the three experiments are shown in FIG. 16. Digoxin concentrations in clinical sera samples were determined in all three assays in a blind experiment for comparison with results obtained for the same sera in another laboratory (Sheba Government Hospital) with another commercial kit (Diagnostic Products). The data are collected in Table 5.

Similar experiments for comparison data with known kits were performed with various clinical sera and are presented in the Tables 1 to 14.

Table 1. FSH.
Table 2. HPRL (prolactin).
Table 3. Ferritin.
Table 4. Thyroxine.
Table 5. Digoxin.
Table 6. Estradiol.
Table 7. Pregstat.
Table 8. hPL.
Table 9. hLH.
Table 10. Total urinary estrogen.
Table 11. T$_3$.
Table 12. hTg-Ab.
Table 13. TSH.
Table 14. FSH (Biodata kit).

In a similar manner comparison tests were carried out with:
Enzyme immunoassay HPL nosticon eliza system, and
solid phase GENTAMISIN fluorescence immunoassay.

TABLE 1

Comparison of FSH clinical sera values (mIU/ml) obtained with kit protocol (centrifugation) and Lidex PS methodology.

| SERUM CODE | HYPOLAB KIT PROTOCOL | LIDEX PROTOCOL |
|---|---|---|
| M 9 | 15.67 | 16.03 |
| L + | 3.75 | 3.47 |
| H | 59.48 | 57.59 |
| H (1:2) | 59.68 | 53.45 |

TABLE 1-continued

Comparison of FSH clinical sera values (mIU/ml) obtained with kit protocol (centrifugation) and Lidex PS methodology.

| SERUM CODE | HYPOLAB KIT PROTOCOL | LIDEX PROTOCOL |
|---|---|---|
| ♀ menop. | 47.19 | 37.15 |
| ♀ menop. 1:2 | 53.10 | 37.04 |
| ♀ menop. 1:4 | 50.04 | 44.04 |
| ♀ | 6.10 | 7.01 |
| ♀ | 0.61 | 0.62 |
| ♂ 1 | 3.07 | 3.32 |
| ♂ 7 | 4.19 | 5.19 |
| LHRH Stm 0' | 8.11 | 9.10 |
| LHRH Stm 30' | 11.69 | 10.78 |
| LHRH Stm 60' | 14.98 | 14.35 |
| Ortho III | 5.69 | 4.31 |
| Ortho IV | 4.21 | 3.84 |
| Ortho 10T10 2A | 9.26 | 11.87 |
| Ortho 10T10 2B | 4.45 | 4.62 |
| Ortho 10T10 2C | 3.64 | 2.77 |

TABLE 2

Comparison of HPRL clinical sera values (ng/ml) obtained with kit protocol (centrifugation) and Lidex PS methodology.

| SERUM CODE | HYPOLAB KIT PROTOCOL | LIDEX PROTOCOL |
|---|---|---|
| M 9 | 11.68 | 13.96 |
| M 7 | 10.00 | 9.67 |
| L | 4.07 | 5.08 |
| H | 76.42 | 100.77 |
| H (1:2) | 75.64 | 79.80 |
| ♂ | 2.40 | 2.65 |
| ♂ | 5.28 | 6.18 |
| ♀ | 4.02 | 4.43 |
| ♀ | 9.94 | 10.73 |
| menop. ♀ | 7.31 | 7.71 |
| menop. ♀ | 4.70 | 6.78 |
| Ortho-Ligand | | |
| 10T10 2A | 1.89 | 1.90 |
| 10T10 2B | 1.58 | 1.53 |
| 10T10 2C | 1.84 | 2.76 |

TABLE 3

Comparison of ferritin clinical sera values (ng/nl) obtained with kit protocol (centrifugation) and with lidex PS methodology.

| SERUM NO. | HYPOLAB KIT PROTOCOL | LIDEX PROTOCOL |
|---|---|---|
| 1 | <20 | <20 |
| 2 | <20 | <20 |
| 3 | 71.4 | 70.3 |
| 4 | 32.1 | 36.3 |
| 5 | 135.7 | 131 |
| 6 | 56.7 | 65.4 |
| 7 | <20 | <20 |
| 8 | <20 | <20 |

TABLE 4

Comparison of thyroxine clinical sera values (μg %) obtained with kit protocol (centrifugation) and with Lidex PS methodology.

| SERUM | HYPOLAB KIT PROTOCOL | LIDEX PROTOCOL |
|---|---|---|
| M 9 | 6.76 | 6.62 |
| L | 1.70 | 1.30 |
| M | 22.44 | 20 |
| Plasma-5 | 9.66 | 9.80 |
| Plasma-18 | 16.84 | 17.80 |
| Plasma-6 | 9.76 | 10.58 |
| Plasma-30 | 5.05 | 4.53 |
| Plasma-20 | 7.00 | 7.75 |
| Ortho-Ligand | | |
| 10T10 2A | 0.61 | 0.67 |
| 10T10 2B | 7.24 | 6.74 |
| 10T10 2C | 13.61 | 15.25 |

TABLE 5

Comparison of Diogoxin clinical sera values (ng/ml) obtained with kit protocol (centrifugation); lidex LS (solvent extraction); lidex PS methodology and (independently) Sheba Hospital Laboratory (different kit with centrifugation).

| | Digoxin concentration (ng/ml) | | | |
|---|---|---|---|---|
| SERUM NO. | BECTON-DICKINSON ASSAY DIRECTIONS | LIDEX PS (Membrane) | LIDEX LS (solvent extraction) | Sheba Hospital (Diagnostic Products) Assay Directions |
| 1 | 0.5 | 0.3 | 0.5 | 0.4 |
| 2 | 1.8 | 2.3 | 1.9 | 2.2 |
| 3 | 0.7 | 0.9 | 0.9 | 1.0 |
| 4 | 0.5 | 0.7 | 0.6 | 0.6 |
| 5 | 1.4 | 1.5 | 1.6 | 1.6 |
| 6 | 1.0 | 1.4 | 1.4 | 1.3 |
| 7 | 0.3 | 0.7 | 0.7 | 0.5 |
| 8 | 0.7 | 1.1 | 1.2 | 1.4 |
| 9 | 4.1 | 4.1 | 3.4 | 5.7 |

TABLE 6

Comparison of Estradiol clinical sera values (pg/ml) with Biodata kit protocol and Lidex methodology.

| ASSAY SYSTEM | BIODATA 20% PEG | LIDEX PEG 8%/DAB | REFERENCE VALUES |
|---|---|---|---|
| MAX. BINDING (%) | 32.2 | 29.0 | 45 |
| N.S.B. | 3.7 | 6.9 | 9.5 |
| CONCENTRATIONS | STANDARD CURVE | | |
| 31.2 pg/ml | 70.0 | 68.4 | |
| 62.5 pg/ml | 68.0 | 57.5 | |
| 125.0 pg/ml | 54.7 | 50.1 | |
| 250 pg/ml | 42.2 | 40.7 | |
| 500 pg/ml | 34.3 | 33.2 | |
| 1000 pg/ml | 28.9 | 24.7 | |
| 2000 pg/ml | 19.7 | 19.3 | |
| CLINICAL SAMPLES | | | |
| SEROTEST | 374.2 Br.S.56 | 477.5 Br.S.57 | 500 |

TABLE 7

Comparison of Preg/stat clinical sera values obtained with Serono kit protocol and Lidex methodology.

| | Serono Kit | LIDEX PEG/DAB Serono | LIDEX 8% PEG/DAB | REMARKS |
|---|---|---|---|---|
| Max. bind | 40.7% | 41.3% | 44.1% | |
| C.R. | 1.19 | 1.23 | 1.18 | |
| 1 | 0.93 | 0.94 | 1.06 | — |
| 2 | 0.96 | 0.99 | 1.03 | — |
| 3 | 0.96 | 0.97 | 1.0 | — |
| 4 | 0.94 | 0.97 | 0.99 | — |
| 5 | 0.98 | 1.0 | 1.03 | — |
| 6 | 0.96 | 0.99 | 1.01 | — |
| 7 | 0.97 | 0.99 | 0.97 | — |
| 8 | 1.11 | 1.12 | 1.13 | intermediate |
| 9 | 1.12 | 1.16 | 1.19 | intermediate |
| 10 | 1.31 | 1.35 | 0.94 | + |
| 11 | 1.81 | 1.92 | 0.92 | + |
| 12 | 3.46 | 4.54 | 5.05 | + |
| 13 | 3.58 | 4.76 | 4.41 | + |
| 14 | 1.35 | 1.43 | 1.48 | + |
| 15 | 1.81 | 1.93 | 1.15 | + |
| 16 | 1.46 | 1.61 | 1.74 | + |

TABLE 8

Comparison of hPL clinical sera values (ng/ml) with Hypolab kit protocol and Lidex methodology.

| ASSAY SYSTEM | HYPOLAB PEG 11% | LIDEX PEG 8%/DAB | REFERENCE VALUES |
|---|---|---|---|
| MAX. BINDING (%) | 69.8 | 73.8 | 65.7 |
| N.S.B. | 5.7 | 6.4 | 4.1 |
| CONCENTRATIONS | STANDARD CURVE | | |
| 12.5 ng/ml | 102 | 94.2 | |
| 25 ng/ml | 90.4 | 83.2 | |
| 50 ng/ml | 79.1 | 73.8 | |
| 100 ng/ml | 62 | 62 | |
| 200 ng/ml | 42 | 40 | |
| 400 ng/ml | 26.5 | 26 | |
| 800 ng/ml | 17 | 14.5 | |
| CLINICAL SAMPLES | | | |
| SERO TEST | 94.7 | 77.9 | 89.1 |
| 1 | >800 | >800 | >800 |
| 2 | 8.1 | 15.6 | |
| 3 | 16.2 | 19.0 | |
| 4 | >800 | >800 | |
| 5 | 66.5 | 98 | |
| 6 | 68.0 | 61.3 | |

TABLE 9

Comparison of H1H clinical sera values (mlu/ml) obtained with Hypolab Kit protocol and Lidex methodology.

| ASSAY SYSTEM | HYPOLAB | LIDEX PEG 8%/DAB | REFERENCE VALUES | |
|---|---|---|---|---|
| MAX. BINDING (%) | 23.6 | 28.8 | 39.2 | |
| N.S.B. | 2.0 | 5.5 | 1.7 | |
| CONCENTRATIONS | STANDARD CURVE | | | |
| 2 mIU/ml | 85.7 | 89.9 | | |
| 5 mIU/ml | 63.9 | 69.6 | | |
| 10 mIU/ml | 49.0 | 51.3 | | |
| 20 mIU/ml | 34.4 | 33.7 | | |
| 40 mIU/ml | 21.1 | 22.3 | | |
| 100 mIU/ml | 5.5 | 7.2 | | |
| CLINICAL SAMPLES | | | | |
| SEROTEST | 22.4 | 19.13 | 17.2 | |
| a 147 | 13.6 | 14.2 | 2.7 | divide by 1.5 |
| b 170 | 49.5 | 58.0 | 64.5 | |
| c 180 | 51.5 | 32.6 | 90 | |
| d | 4.29 | 9.28 | | |
| e 197 | 4.2 | 5.7 | 6.9 | |
| f 202 | 12.1 | 11.2 | 16.5 | |
| g 205 | 26.2 | 25.73 | 39.8 | |
| h 219 | 6.93 | 8.8 | 11.4 | |
| i 228 | 2.8 | 3.4 | 5.3 | |
| j 230 | 2.3 | 3.3 | 2.8 | |

TABLE 10

Comparison of T.U.E. (Total Urine Estrogens) clinical sera values (ng/ml) with Hypolab kit protocol and Lidex methodology.

| ASSAY SYSTEM | HYPOLAB Carrier Serum + PEG 20% | LIDEX PEG 8%/DAB | REFERENCE VALUES |
|---|---|---|---|
| MAX. BINDING (%) | 39.4 | 22.8 | 35.9 |
| N.S.B. | 3.8 | 4.2 | 3.8 |
| CONCENTRATIONS | STANDARD CURVE | | |
| 0.5 ng/ml | 82.8 | 83.6 | |
| 1 ng/ml | 71.6 | 75.3 | |
| 2 ng/ml | 62.6 | 64.2 | |
| 4 ng/ml | 33.4 | 37.5 | |
| 8 ng/ml | 14.6 | 16.1 | |
| 16 ng/ml | 7.2 | 8.5 | |
| CLINICAL SAMPLES | | | |
| SEROTEST | 47.3 | 44.9 / 29.4 / 48.0 | 38.0 (MEAN) |
| female | 54.82 | 49.14 | |
| male | 47.1 | 42.6 | |

TABLE 11

Comparison of T-3 clinical sera values (ng/ml) with Biodata kit protocol and Lidex methodology.

| ASSAY SYSTEM | BIODATA PEG 20% | LIDEX PEG 8%/DAB |
|---|---|---|
| MAX. BINDING (%) | 62.9% | 60.2% |
| N.S.B. | 2.0% | 4.4 |
| CONCENTRATIONS | STANDARD CURVE | |
| 0.125 ng/ml | 96.2 | 96.0 |
| 0.25 ng/ml | 92.6 | 94.5 |
| 0.5 ng/ml | 82.1 | 83.2 |
| 1.0 ng/ml | 59.9 | 61.9 |
| 2.0 ng/ml | 42.7 | 38.9 |
| 4.0 ng/ml | 25.9 | 26.1 |
| 8.0 ng/ml | 13.4 | 14.3 |
| CLINICAL SAMPLES | | |
| SEROTEST DIL 1.2 | 0.82 / 1.02 ng/ml | 0.68 / 0.6 ng/ml |
| a | 0.97 | 0.96 |
| b | 0.52 | 0.71 |
| c | 0.77 | 0.92 |
| d | 1.34 | 1.33 |
| e | 0.69 | 0.68 |
| f | 0.86 | 0.95 |

NORMAL VALUES: 0.6–1.7 ng/ml.

TABLE 12

Comparison hTg-Ab clinical sera values with Hypolab kit protocol and Lidex methodology.

| ASSAY | HYPOLAB CORR. COUNTS | % BIND- | LIDEX CORR. COUNTS | % BIND- |
|---|---|---|---|---|

TABLE 12-continued

Comparison hTg-Ab clinical sera values with Hypolab kit protocol and Lidex methodology.

| SYSTEM | MEAN$_{CPM}$ | ING | MEAN$_{CPM}$ | ING |
|---|---|---|---|---|
| T.C. | T.C. 18889.55 | | T.C. 18887.9 | |
| CONCENTRATIONS | | | STANDARD CURVE | |
| 1:1 | 1686.2 | 8.9% | 2625.7 | 13.9% |
| 1:20 | 2014.6 | 10.6% | 3902.5 | 20.6% |
| 1:100 | 2917.05 | 15.4% | 5982.25 | 31.6% |
| 1:1000 | 3326.95 | 17.6% | 7120.85 | 37.7% |
| 1:10000 | 5245.35 | 27.7% | 8347.35 | 44.1% |
| 1:20000 | 6269.2 | 33.1% | 9102.55 | 48.1% |
| 1:50000 | 7324.25 | 38.7% | 9239.1 | 48.9% |
| CLINICAL SAMPLES | | | | |
| P.C. | 4726.9 | 25.02 | 7891.5 | 41.7% |
| N.C. | 886.9 | 4.6 | 1880.15 | 9.9% |
| a | 1650.15 | 8.7 | 1540.45 | 8.1% |
| b | 1570.96 | 8.3 | 1955.9 | 10.3% |
| c | | | 1777.25 | 9.4% |

TABLE 13

Comparison of TSH clinical sera values ($\mu$IU/ml) with Hypolab kit protocol and Lidex methodology.

| ASSAY SYSTEM | HYPOLAB DAB/H$_2$O | LIDEX PEG 8%/ DAB | REFERENCE VALUES |
|---|---|---|---|
| MAX. BINDING (%) | 40.3% | 41.8% | 58.6% |
| N.S.B. | 2.0% | 4.8% | 2.3% |
| CONCENTRATIONS | | STANDARD CURVE | |
| 0.62 $\mu$IU/ml | 98.6 | 95.8 | |
| 1.25 $\mu$IU/ml | 85.7 | 87.2 | |
| 2.5 $\mu$IU/ml | 76.3 | 78.6 | |
| 5.0 $\mu$IU/ml | 49.7 | 59.8 | |
| 10.0 $\mu$IU/ml | 28.1 | 29.8 | |
| 20.0 $\mu$IU/ml | 14.0 | 18.2 | |
| CLINICAL SAMPLES | | | |
| SEROTEST | 4.62 | 7.94 | 5.1 |
| Dil 1:2 | 4.2 | 4.37 | 4.4 |
| | HYPOLAB $\mu$IU/ml | LIDEX $\mu$IU/ml | |
| a | 2.06 | 2.41 | |
| b | 1.78 | 1.98 | |
| c | 2.91 | 3.05 | |
| d | 2.86 | 3.3 | |
| e | 2.06 | 2.23 | |
| f | 1.58 | 1.99 | |

TABLE 14

Comparison of FSH clinical sera values (mIu/ml) with Biodata kit protocol and Lidex methodology.

| | BIODATA PEG 11%/DAB | LIDEX PEG 8%/DAB Serono | ref. value RAMBAN/ HYPOLAB |
|---|---|---|---|
| a 151 | 2.79 | 3.53 | 2.7 |
| b 168 | 8.78 | 9.48 | 6.6 |
| c 227 | 6.55 | 6.73 | 5.6 |
| d 228 | 5.97 | 7.51 | 5.6 |
| e 256 | 31.9 | 34.74 | 34 |
| f 268 | 81.18 | 72.75 | 60 |
| g 277 | 33.17 | 31.0 | 25 |
| h 651 | 2.4 | 2.66 | — |
| i 658 | 1.39 | 2.56 | 2 |
| j 661 | 1.98 | 2.64 | 2.4 |
| k 681 | 8.98 | 10.56 | 7.8 |

We claim:

1. A method for carrying out an immunoassay with a liquid-liquid extraction using a first liquid which is substantially immiscible with a second liquid, said method being carried out in a device comprising a mixing reservoir; a mixer-separator means, snuggly fitted into said mixing reservoir for sliding movement therein and having at least one unobstructed channel traversing the vertical axis thereof and opening into said mixing reservoir; and a collection container at the end of said mixer-separator means opposite said unobstructed opening, for thoroughly mixing the two liquids in response to at least one movement of said mixer-separator means into and out of said mixing reservoir by an amount sufficient to cause a substantial portion of both liquids to be transported through said channel into said collection container and back into said mixing reservoir and for subsequently separating the first liquid from the second liquid in response to controlled movement of said mixer-separator means into said mixing reservoir to a distance sufficient to transport the desired amount of the less dense liquid through said channel into said collection container; and a stopper means on said collection container for selectively opening and closing said collection container to the outside, said method comprising the steps of:
(a) arranging a plurality of the mixing reservoirs in a rack designed to hold a number of said mixing reservoirs;
(b) introducing a reagent and analyte and at least one substantially immiscible extracting liquid into each of said mixing reservoirs;
(c) capping each of said mixing reservoirs with one of said mixer-separator means;
(d) allowing the reagents and analytes to incubate for a required period of time in the mixing reservoirs capped with the mixer-separator means;
(e) placing the rack carrying the capped devices with the incubated reagents and analytes into a press-device designed to perform at a controlled rate a downward and upward movement whereby the mixer separator means are reciprocated in the mixing reservoirs at a chosen rate and for a preselected distance sufficient to complete the desired mass-transport and separation operations;
(f) operating the downward movement of said press-device at the preselected rate and distance sufficient to separate the upper immiscible phase from the lower phase;
(g) removing the rack upon the disengagement of the press-device; and
(h) placing the separator devices into the desired analytical instrument for a quantitative or qualitative measurement of either one, or both, of the separated phases.

2. A method according to claim 1, comprising a radioimmunoassay method.

3. A method according to claim 1, comprising a metalloimmunoassay.

4. A method according to claim 1, comprising a fluorescence assay.

5. A method according to claim 1, wherein the press device is built in the form of a closed press in which the movement of the pressing plate is produced by a motor.

6. The method according to claim 1, wherein the rack includes means for permitting maximum visualization of the mixing reservoir during the assay.

7. A method according to claim 1, carried out in an automatic manner.

8. A method according to claim 1, comprising carrying-out said immunoassay for the determination of an antigen, a hormone, a barbiturate, a steroid, a vitamin, a tranquilizer, a drug or an alkaloid.

9. A method according to claim 8, comprising a determination of FSH.

10. A method according to claim 8, comprising a determination of HPRL.

11. A method according to claim 8, comprising a determination of Ferritin.

12. A method according to claim 8, comprising a determination of Thyroxine.

13. A method according to claim 8, comprising a determination of Digoxin.

14. A method according to claim 8, comprising a determination of Estradiol.

15. A method according to claim 8, comprising a determination of Pregstat.

16. A method according to claim 8, comprising a determination of hPL.

17. A method according to claim 8, comprising a determination of total urinary estrogen.

18. A method according to claim 8, comprising a determination of $T_3$.

19. A method according to claim 8, comprising a determination of ATg-Ab.

20. A method according to claim 8, comprising a determination of TSH.

21. A method according to claim 8, comprising an enzyme immunoassay of HPL nosticon eliza.

22. A method according to claim 8, comprising a solid phase GENTAMISIN fluorescence immunosay.

* * * * *

Disclaimer 4,456,690.—*Michael Cais* and *Moshe Shimoni*, Haifa, Israel. NON-CENTRIFUGATION METHOD FOR IMMUNOASSAY OF MATERIALS. Patent dated June 26, 1984. Disclaimer filed Sept. 4, 1984, by the assignee, *Technion Research and Development Foundation Ltd.*

The term of this patent subsequent to June 12, 2001 has been disclaimed.
[*Official Gazette February 26, 1985.*]